US008299271B2

(12) United States Patent
Wu et al.

(10) Patent No.: US 8,299,271 B2
(45) Date of Patent: Oct. 30, 2012

(54) SOLID TARTRATE SALTS OF DPP-IV INHIBITORS

(75) Inventors: Zhen-Ping Wu, La Jolla, CA (US); David Alan Campbell, San Diego, CA (US); Julie M. Cherrington, La Jolla, CA (US)

(73) Assignee: Phenomix Corporation, Encinitas, CA (US)

( * ) Notice: Subject to any disclaimer, the term of this patent is extended or adjusted under 35 U.S.C. 154(b) by 553 days.

(21) Appl. No.: 12/439,140

(22) PCT Filed: Aug. 23, 2007

(86) PCT No.: PCT/US2007/018629
§ 371 (c)(1),
(2), (4) Date: Jul. 20, 2009

(87) PCT Pub. No.: WO2008/027273
PCT Pub. Date: Mar. 6, 2008

(65) Prior Publication Data
US 2010/0323988 A1 Dec. 23, 2010

Related U.S. Application Data

(60) Provisional application No. 60/841,097, filed on Aug. 30, 2006.

(51) Int. Cl.
*C07D 207/00* (2006.01)
(52) U.S. Cl. .................................................... 548/405
(58) Field of Classification Search ............... 548/405, 548/412, 416
See application file for complete search history.

(56) References Cited

U.S. PATENT DOCUMENTS

| 7,317,109 B2 * | 1/2008 | Campbell et al. ............. 548/405 |
| 7,674,913 B2 * | 3/2010 | Campbell et al. ............. 548/405 |
| 2006/0264400 A1 | 11/2006 | Campbell et al. |
| 2007/0060547 A1 | 3/2007 | Campbell et al. |

FOREIGN PATENT DOCUMENTS

| CL | 24952007 A1 | 4/2008 |
| CL | 25132007 A1 | 4/2008 |
| CL | 25112007 A1 | 5/2008 |
| SG | 174754 | 10/2011 |
| WO | WO-2005047297 A1 | 5/2005 |
| WO | WO 2005047297 A1 * | 5/2005 |
| WO | WO-2007016356 A1 | 2/2007 |
| WO | WO-2008027273 A2 | 3/2008 |
| WO | WO-2008027273 A3 | 3/2008 |
| WO | WO-2008109681 A2 | 9/2008 |

OTHER PUBLICATIONS

"Chilean Application Serial No. 2499-2007, Office Action mailed Dec. 14, 2010", 4 pgs.
"Chilean Application Serial No. 2499-2007, Response filed Aug. 18, 2010", 3 pgs.
"Chinese Application Serial No. 200780036564.9, Office Action mailed Mar. 9, 2011", 10 Pgs.
"Eurasian Application Serial No. 200900375, Office Action mailed Dec. 7, 2010", 3 pgs.
"Eurasian Application Serial No. 200900375, Office Action Response Filed Mar. 9, 2011", 2 pgs.
"European Application Serial No. 07837254.7, Extended European Search Report mailed May 17, 2011", 6 pgs.
"International Application Serial No. PCT/US2007/018629, Preliminary Report on Patentability mailed Dec. 9, 2008", 10 pgs.
"Israel Application Serial No. 197225, Office Action mailed Apr. 3, 2011", 1 pg.
"New Zealand Application Serial No. 575756, Response filed Jan. 25, 2011 to Office Action mailed Aug. 13, 2010", 13 pgs.
"New Zealand Application Serial No. 575756, Subsequent Examiner Report mailed Feb. 21, 2011", 2 pgs.
"New Zealand Application Serial No. 575756, Subsequent Examiner Response sent to client Apr. 5, 2011", 3 pgs.
"Taiwanese Application Serial No. 096132256, Response filed Jun. 18, 2010", 9 pgs.
Li, X., et al., "Preclinical Development of PHXI149, an Orally Available, Potent and Selective DPP4 (Dipeptidyl Peptidase) Inhibitor", American Diabetes Association, 66th Scientific Sessions Meeting, [Online]. Retrieved from the Internet: <URL: http://professional.diabetes.org/Abstracts_Display.aspx?TYP=1&CID=47419>, (retrieved on Apr. 6, 2011), 4 pgs.
Taiwan Application Serial No. 096132256, Office Action mailed May 19, 2010 (English translation), 4 pgs.
"Chinese Application Serial No. 200780036564.9, Response filed Jul. 25, 2011 to Office Action mailed Mar. 9, 2011", 3 pgs.
"Chilean Application Serial No. 2499-2007, Office Action Mailed Jul. 7, 2010", 3 pgs.
"Chilean Application Serial No. 2499-2007, Office Action Response Filed: Aug. 31, 2010", 3 pgs.
"Israeli Patent Application No. 197225, Office Action Response filed Sep. 19, 2010", 1 pg.
"New Zealand Application Serial No. 575756, First Examiner Report mailed Aug. 13, 2010", 2 pgs.
"Taiwanese Application Serial No. 096132256, Final Office Action mailed Sep. 9, 2010", 6 pgs.
"Taiwanese Application Serial No. 096132256, Office Action Response filed Jul. 9, 2010", 9 pgs.
"International Application Serial No. PCT/US2007/018629, Search Report mailed Jun. 3, 2008.", 6 pgs.
"International Application Serial No. PCT/US2007/018629, Written Opinion mailed Jun. 3, 2008.", 2 pgs.
Eurasian Application Serial No. 200900375, Office Action mailed Sep. 8, 2011, Statement from Russian Patent Agent sent Sep. 8, 2011, and Letter from U.S. Patent Attorney mailed Dec. 27, 2011, 7 pgs.
European Application Serial No. 07837254.7, Extended European Search Report Response filed Dec. 14, 2011, 10 pgs.
O'Farrell, Anne-Marie, et al., "Pharmacokinetic and pharmacodynamic assessments of the dipeptidyl peptidase-4 inhibitor PHX1149: double-blind, placebo-controlled, single-and multiple-dose studies in healthy subjects", Clinical Ther., vol. 29(8), http://www.ncbi.nlm.nih, (2007), 1692-1705.

(Continued)

*Primary Examiner* — Kevin E Weddington
(74) *Attorney, Agent, or Firm* — Schwegman Lundberg & Woessner, P.A.

(57) ABSTRACT

This invention relates to DPP-IV inhibitory citrate or tartrate salts of pyrrolidinylaminoacetyl pyrrolidine boronic acid compounds that are physically and chemically stable, substantially non-deliquescent solids under ambient conditions.

3 Claims, 9 Drawing Sheets

OTHER PUBLICATIONS

"Australian Application Serial No. 2007290684, Response filed Jul. 23, 2012 to Office Action mailed May 15, 2012", 13 pgs.

"Canadian Application Serial No. 2,661,776, Voluntary Amendment filed Aug. 17, 2012", 4 pgs.

"Eurasian Application Serial No. 200900375, Office Action mailed Jun. 27, 2012", 3 pgs.

"Eurasian Application Serial No. 200900375, Response filed Jul. 25, 2012 to Office Action mailed Jun. 27, 2012", 1 pg.

"Korean Application Serial No. 10-2009-7006270, Amendment filed Aug. 23, 2012".

* cited by examiner

SOLID TARTRATE SALTS OF DPP-IV INHIBITORS

CLAIM OF PRIORITY TO RELATED APPLICATIONS

This application is a U.S. National-Stage entry under 35 U.S.C. §371 based on International Application No. PCT/US2007/018629, filed Aug. 23, 2007 and published in English as WO 2008/027273 on Mar. 6, 2008, which designates the United States of America, and claims the priority of U.S. provisional application Ser. No. 60/841,097, filed Aug. 30, 2006, which are incorporated herein by reference in their entirety.

FIELD OF THE INVENTION

The field of the invention is novel solid salt forms of certain selective inhibitors of dipeptidyl peptidase IV. The invention relates to tartrate and citrate salts of pyrrolidinylaminoacetyl pyrrolidine boronic acid compounds, potent and selective inhibitors of DPP-IV. These novel salts, which are chemically and physically stable over at least a 12 month period, are substantially non-deliquescent solids and are suitable for formulation as medicaments.

BACKGROUND OF THE INVENTION

Dipeptidyl peptidase-IV (DPP-IV) is a serine protease that belongs to a group of amino-dipeptidases that includes DPP-VII, DPP-VIII, DPP-IX, and fibroblast activation protein (FAP). DPP-IV, which catalyzes the release of an N-terminal dipeptide from proteins, is believed to play a role in the control of glucose metabolism. In vivo administration of synthetic inhibitors of DPP-IV prevents N-terminal degradation of the insulinotropic hormone glucagon like peptide-1 (GLP-1) and gastric inhibitory peptide (GIP) resulting in increased insulin secretion and improved glucose tolerance. Substituted aminoacetyl pyrrolidine boronic acids have been developed as inhibitors for the treatment of patients with impaired glycemic control such as Diabetes Mellitus and related conditions. Consequently, it is desirable to formulate such inhibitors as convenient-to-use solid pharmaceutical materials. Free bases and salts of many pharmaceutical compounds are such typical pharmaceutical formulations. However, the free base forms of some aminoacetyl pyrrolidine boronic acids are not stable solids, readily absorbing atmospheric moisture. In addition, some salts of these free bases are likewise not stable solids.

U.S. application Ser. No. 10/514,575, filed Nov. 15, 2004, titled "Heterocyclic Boronic Acid Compounds," and published on Mar. 15, 2007 as US 2007/0060547, discloses a large class of pyrrolidine boronic acid compounds that inhibit dipeptidyl peptidase-IV. In addition, U.S. Provisional Application Ser. No. 11/381,085, filed May 1, 2006, titled "Pyrrolidine Compounds and Methods for Selective Inhibition of Dipeptidyl Peptidase-IV," and published on Nov. 23, 2006 as US 2006/0264400, discloses a more specific class of pyrrolidinylaminoacetyl pyrrolidine boronic acid compounds that selectively inhibit DPP-IV. One embodiment of that invention shows particular promise as a medicament. However, although biologically effective as a free base, the free base compound is not physically or chemically stable as a solid on storage.

Therefore, there is a need for a chemically stable salt form of the compound for use in pharmaceutical formulations for treatment of malconditions wherein selective inhibition of DPP-IV is medically indicated.

SUMMARY OF THE INVENTION

The present invention concerns physically and chemically stable organic salt forms of DPP-1V inhibitory pyrrolidinylaminoacetyl-pyrrolidine-2-boronic acids, compounds of formula (I) as defined herein. The citrate and tartrate salts of compounds of formula (I) are substantially non-deliquescent solids and can be stored under ambient conditions for at least 12 months without decomposition. The solid forms of these compounds are suitable for processing, formulation, storage, and administration of the DPP-IV inhibitors, which can be useful as orally ingested medicaments for the treatment of diabetes. Methods of preparing the salt forms, methods of using the salt forms, pharmaceutical compositions including the salt forms, and pharmaceutical combinations including the salt forms, are also provided.

An embodiment according to the invention provides a citrate or tartrate salt of a pyrrolidine compound of formula (I):

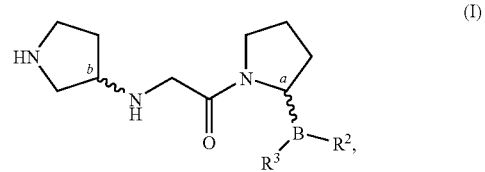

a cyclic isomer thereof or any hydrate or solvate thereof; wherein $R^2$ and $R^3$ independently are —OH, —O⁻M⁺ wherein M⁺ is a cation, a hydroxyl bearing a boronic acid protecting group, or a group capable of being hydrolyzed to a hydroxyl group in an aqueous solution at physiological pH or in biological fluids; or $R^2$ and $R^3$ together with the boron atom to which they are attached form a cyclic group capable of being hydrolyzed to a boronic acid group; the wavy lines at asymmetric carbons $C^a$ and $C^b$ independently indicate for each asymmetric carbon an R configuration, an S configuration, or a mixture of both configurations, such that all stereoisomers and all stereomeric mixtures are included; and the tartrate moiety has any stereomeric configuration or mixture thereof.

In an embodiment of the invention, the tartrate moiety can be an L-tartrate, a D-tartrate, a meso-tartrate, or any combination thereof. In another embodiment, the tartrate moiety is an L-tartrate.

In an embodiment, the $R^2$ and $R^3$ groups can both be hydroxyl groups, such that the boron atom is contained in a boronic acid group bonded to the pyrrolidine 2-position, thus, a boro-proline moiety. In another embodiment, $R^2$ and $R^3$ of formula (I) can both be hydroxyl groups and the tartrate salt be an L-tartrate salt.

In an embodiment, the claimed salt can be any hydrate or solvate thereof.

Another embodiment is directed to cyclic isomer of formula (V):

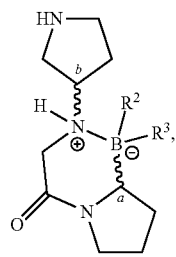

wherein $C^a$ and $C^b$ each independently has an R configuration, an S configuration, or a mixture of both configurations such that all stereoisomers and all stereomeric mixtures are included.

Another embodiment is directed to an L-tartrate salt of a compound of formula (V). Yet another embodiment is directed to an L-tartrate salt of a compound of formula (V) wherein $R^2$ and $R^3$ are both hydroxyl groups.

Another embodiment of the invention is directed to a citrate or tartrate salt of a compound of formula (IA):

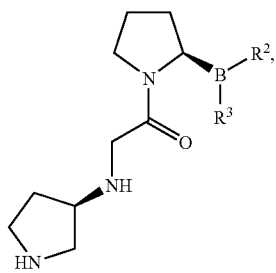

wherein the stereomeric purity is at least about 55%, or at least about 90%, or at least about 98%. An embodiment provides a salt wherein $R^2$ and $R^3$ are both hydroxyl groups. Another embodiment provides an L-tartrate salt of the compound of formula (IA). Another embodiment provides an L-tartrate salt of the compound of formula (IA) wherein $R^2$ and $R^3$ are both hydroxyl groups.

Another embodiment of the invention is directed to a citrate or tartrate salt of a compound of (IB):

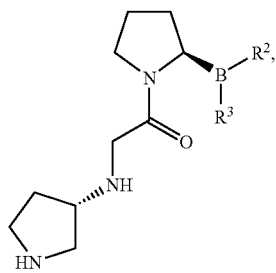

wherein the stereomeric purity is at least about 55%, or at least about 90%, or at least about 98%. An embodiment provides a salt wherein $R^2$ and $R^3$ are both hydroxyl groups. Another embodiment provides an L-tartrate salt of the compound of formula (IB). Another embodiment provides an L-tartrate salt of the compound of formula (IB) wherein $R^2$ and $R^3$ are both hydroxyl groups.

Another embodiment of the invention provides substantially non-deliquescent solid forms of the citrate and tartrate salts of compounds of any one of formulas (I), (IA), (IB), or (V), or cyclic forms, hydrates, or solvates thereof.

An embodiment of the invention also is directed to a pharmaceutical composition containing a citrate or tartrate salt of the invention and a pharmaceutically acceptable carrier. The pharmaceutical composition may be formulated to be dosed by any administrative route including but not limited to parenteral injection, oral, buccal, rectal and the like.

An embodiment of the invention is directed to a method of treatment of a malcondition that can be regulated or normalized via inhibition of DPP-IV. The method involves administration of an effective amount of a citrate or tartrate salt of the invention to mammals, such as humans, to affect a malcondition that can be regulated or normalized via inhibition of DPP-IV.

An embodiment of the invention is directed to a pharmaceutical combination of a citrate or tartrate salt of the invention and one or more other medicaments that increases insulin secretion, increases insulin sensitivity, reduces the uptake of sugar from the gastrointestinal track, enhances the effect of endogenous peptides or proteins that affect glycemic control, provides a replacement for endogenous peptides or proteins that affect glycemic control, or any combination thereof. The pharmaceutical combination may be formulated according to the invention as a pharmaceutical composition.

The invention is also directed to a process for preparing a citrate or tartrate salt of the invention, a method for preparing a pharmaceutical composition of the invention, and the use of a citrate or tartrate salt of the invention in a method for the preparation of a medicament for treating a malcondition that can be regulated or normalized via inhibition of DPP-IV.

DETAILED DESCRIPTION OF THE INVENTION

Definitions

Figure 1:
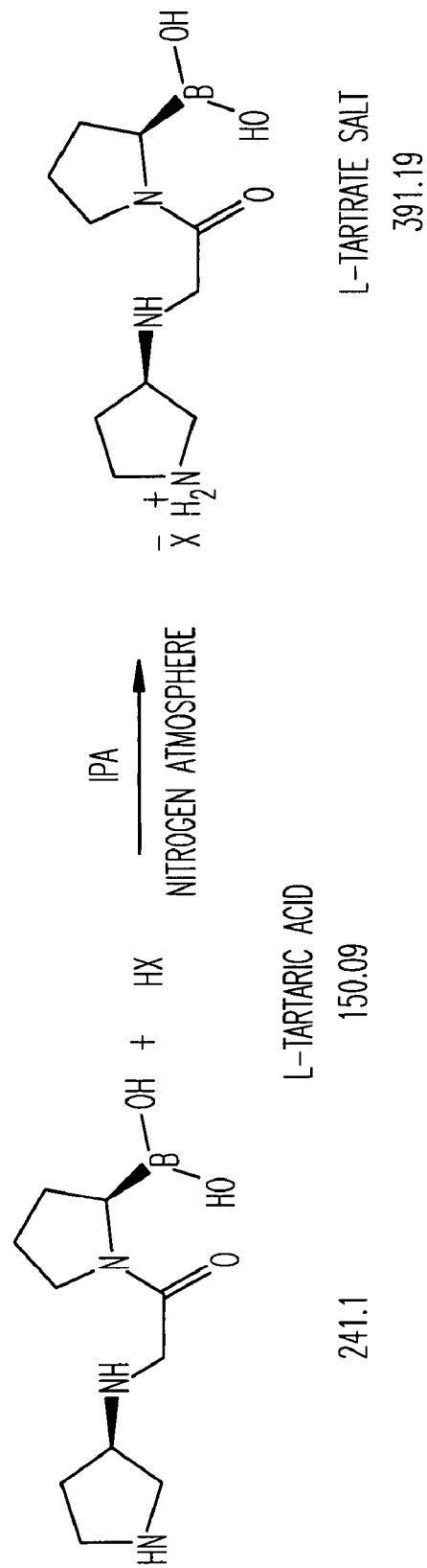
FIG. 1 is a schematic diagram illustrating the formation of the L-tartrate salt of (2R)-1-{7-[(9R)-pyrrolidin-9-ylamino]-acetyl}-pyrrolidine-2-boronic acid.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. The present specification provides selected definitions of certain terms, and these definitions are preferred relative to other definitions in the event that there are discrepancies. In addition, the materials, methods, and examples are illustrative only and not intended to be limiting.

Other features and advantages of the invention will be apparent from the following detailed description and from the claims.

The term "absolute configuration" in connection with an asymmetric carbon is determined by considering the tetrahedral shape of the asymmetric carbon bonds and assigning a priority of 1 through 4 to each of the groups bound to the asymmetric carbon with the group having the highest atomic number having the first priority. If the tetrahedron is viewed from a side remote from group 4, an R absolute configuration is assigned when groups 1-3 are in a clockwise arrangement, and an S absolute configuration is assigned when groups 1-3 are in a counterclockwise arrangement.

The term "and/or," as used herein, means one member of the named group or any combination thereof. The term "or" is an inclusive "or" unless otherwise indicated.

The term "ambient conditions" includes temperatures ranging from about 15° C. to about 45° C., e.g. 20° C., 25° C., 30° C., 35° C., and relative humidity ranging from about 20% to about 65%, e.g. 25%, 30%, 35%, 40%, 45%, 50%, 55%, and 60%.

The term "asymmetric carbon" means a carbon atom covalently bound to four different groups.

The term "beta cell degeneration" is intended to mean loss of beta cell function, beta cell dysfunction, and death of beta cells, such as necrosis or apoptosis of beta cells.

The term "Diabetes Mellitus and related conditions" refers to Type 1 diabetes, Type 2 diabetes, gestational diabetes, MODY, impaired glucose tolerance, impaired fasting glucose, hyperglycemia, impaired glucose metabolism, insulin resistance, obesity, diabetic complications, and the like.

The term "diabetic complications" refers to conditions, diseases and maladies associated with diabetes including retinopathies, neuropathies, nephropathies, cardiomyopathies, dermopathies, arthrosclerosis, coronary artery disease and other known complications of diabetes.

The term "diastereomer" means one member of a group of two or more stereoisomers having at least two asymmetric carbons such that these stereoisomers are not mirror images of each other.

The terms "DPP-VII, DPP-VIM DPP-IX and FAP" mean respectively amino dipeptidyl peptidase VII, VIII, IX and fibroblast activation protein. The DPP enzymes cleave dipeptide moieties at the N-terminus of their protein or oligopeptide substrates. In particular, the term "DPP-IV" denotes dipeptidyl peptidase IV (EC 3.4.14.5; DPP-IV), also known as "CD-26." DPP-IV preferentially cleaves a dipeptide from the N terminus of a polypeptide chain containing a proline or alanine residue in the penultimate position.

The term "enantiomer" means one member of a pair of stereoisomers having the same molecular structure and at least one asymmetric carbon such that the stereoisomers of the pair are the mirror images of each other. If the enantiomer contains two or more asymmetric carbons, the enantiomeric pair will have opposing asymmetry at each asymmetric carbon.

The term "free base" refers to the pyrrolidinylaminoacetyl pyrrolidine boronic acid compound of formula I or V, wherein the amine groups are not protonated.

The term "group that can be hydrolyzed to a hydroxyl" as used herein refers to an ester group formed from the combination of an aliphatic or aromatic alcohol or diol and a boronic acid.

The term "inhibitor" (and its corresponding verb and gerund) means a compound, including a salt thereof, that will reversibly, irreversibly or temporarily interact with an enzyme so as to reduce, modify, slow down or block its enzymatic activity upon its normal substrate. The interaction may occur within or at the enzymatic site or at an allosteric site associated with the enzyme.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. W. Greene, P. G. Wuts, "Protective Groups In Organic Synthesis, $3^{rd}$ Ed." (John Wiley & Sons, New York (1999)), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc) and benzyloxycarbonyl (Cbz).

The term "optically active" means an organic compound containing at least one asymmetric carbon such that a solution of the organic compound will rotate plane polarized light.

The term "optically active mixture" means a mixture of optically active compounds in solution that will rotate plane polarized light. The optically active mixture may be a mixture of diastereomers or an unequal mixture of enantiomers.

The term "prodrug" means a pharmaceutically acceptable compound that will convert to the active ingredient or an active metabolite thereof upon administration of the prodrug to a living organism, preferably a mammal, more preferably a human. The conversion may occur by enzymatic action, chemical hydrolysis, oxidation, reduction or any other in vivo physiological process for chemical or biochemical reaction.

The term "racemic mixture" means an enantiomeric pair of equal proportions such that they cancel each other's rotation of plane polarized light.

As used herein, the phrase "salt of the invention" refers to a citrate salt as well as a tartrate salt of the pyrrolidinylaminoacetyl pyrrolidine boronic acid compound of formula I or V. As used herein, a singular term includes the plural, and likewise, a plural term includes the singular. Thus, the phrase "a salt of the invention" refers to a single stereoisomeric species, the various stereoisomeric species, and mixtures thereof. Non-limiting examples of a salt of the invention include (a) the L-, D-, or meso-tartrate salt of (2R)-1-{7-[(9R)-pyrrolidin-9-ylamino]-acetyl}-pyrrolidine-2-boronic acid and mixtures thereof and (b) the L-, D-, or meso-tartrate salt of (2R)-1-{7-[(9S)-pyrrolidin-9-ylamino]-acetyl}-pyrrolidine-2-boronic acid and mixtures thereof. A salt of the invention also includes the citrate salt of (a) (2R)-1-{7-[(9R)-pyrrolidin-9-ylamino]-acetyl}-pyrrolidine-2-boronic acid; (b) (2R)-1-{7-[(9S)-pyrrolidin-9-ylamino]-acetyl}-pyrrolidine-2-boronic acid; and (c) any combination thereof.

The term "hygroscopic" as the term is used herein refers to a property of a solid substance of spontaneously absorbing water vapor from humid air or gas that is in contact with the substance. A solid substance "deliquesces" or is "deliquescent" when it is hygroscopic and, upon absorption of sufficient water vapor, dissolves in the water it has absorbed.

The term "stereoisomer" means one of the absolute configurations of a single organic molecule having at least one asymmetric carbon. Included within the definition of a stereoisomer are enantiomers and diastereomers. One stereoisomer has one absolute configuration about each of the asymmetric carbons of the organic molecule. An organic molecule with one asymmetric carbon presents two stereoisomers. An organic molecule with two asymmetric carbons presents four stereoisomers. An organic molecule with three asymmetric carbons presents eight stereoisomers. Projecting plane polarized light through a solution containing one stereoisomer will cause rotation of the polarized plane.

The term "stereomeric mixture" means a mixture of two or more stereoisomers and includes enantiomers, diastereomers and combinations thereof. The stereomeric mixture may or may not be optically active.

The term "stereomeric purity" at a given percentage means that the designated stereoisomer predominates at that given percentage in a mixture of stereoisomers.

Unless otherwise specifically stated, the definitions of terms for chemical groups, functional groups, moieties and chemical reactions described herein follow the definitions provided in such organic chemistry textbooks and treatises as "Basic Principles of Organic Chemistry", Roberts and Caserio, W. A. Benjamin & Co. New York, N.Y, 1965; "Advanced Organic Chemistry", 4th edition, Jerry March, Wiley Interscience, New York, N.Y. 1992; T. W. Greene, P. G. Wuts, "Protective Groups In Organic Synthesis, 3rd Ed." (John Wiley & Sons, New York (1999), and Hawley's Condensed Chemical Dictionary, 11th Ed., Sax and Lewis, Van Nostrand, Reinhold, New York, N.Y., 1987. Moreover, the definitions for stereochemical terms are based upon "Stereochemistry of Carbon Compounds", Ernest Eliel, McGraw-Hill publisher, New York, N.Y. 1962. The disclosures of these text books are incorporated herein by reference.

Detailed Description

The citrate or tartrate salts of a compound of formula (I), including cyclic isomers, hydrates and solvates therein, referred to herein as "salts of the invention," have beneficial properties that make them useful, infer alio, in the preparation of pharmaceutical formulations for treatment of diabetes. These properties include, for example, bioactivity for in vivo inhibition of DPP-IV, good yield in preparation, good solubility and rate of dissolution in water or body fluids, and physical and chemical stability under ambient conditions for prolonged periods of time that allow for facile processing, formulation, storage, and administration of the salts of the invention.

The present invention involves the unexpected discovery that a citrate or tartrate salt of a pyrrolidinylaminoacetyl pyrrolidine boronic acid compound, for example, a citrate or tartrate salt of 1-{7-pyrrolidin-9-ylamino]-acetyl}-pyrrolidine-2-boronic acid, a compound of formula (I) which is a selective dipeptidyl peptidase IV inhibitor, has good physical stability as a solid, favorable for processing, formulation, storage, and administration. The free bases of the compounds of formula (I), such as the compounds of formulas (IA) and (IB), and a variety of other salt forms, were found to have poor physical stability under ambient conditions. The free base, and salts of the free base with a variety of organic acids, were found to either be oils or highly deliquescent solids.

Referring to Table 1, below, it is apparent that the free base form and various other salts of the compound of formula (I), wherein $R^2$ and $R^3$ are both hydroxyl, either did not readily form a solid, or if solids were formed, the solids deliquesced at ambient conditions, and thus could not be used for the development of a solid dosage form. The citrate and tartrate salt of the invention readily formed a solid. In addition, the solid did not deliquesce and remained processable under ambient conditions. At room temperature and less than 70% humidity, e.g. at 63% relative humidity, although a salt of the invention can initially absorb some water, the water absorption plateaus and the salt retains its solid powder form at equilibrium, which allows for the development of solid dosage forms. Thus, the citrate and tartrate salts of the invention have desirable physical stability in that although they absorb limited atmospheric water, they remain physically and chemically stable solids. For this reason they are particularly well adapted for the preparation of tablets and capsules, as well as other solid pharmaceutical formulations. These salts of the invention also have good processability in that they are not sticky. Consequently, they can be measured and aliquoted in precise and reproducible amounts. Thus, the salts of the invention have properties that facilitate the preparation of various pharmaceutical formulations. And, as is shown in Table 5, and discussed below, salts of the invention can be stored under ambient conditions in the presence of atmospheric moisture for prolonged periods of time, at least 12 months, without any significant decomposition occurring.

An embodiment of the invention provides a citrate or tartrate salt of a pyrrolidinylaminoacetyl pyrrolidine boronic acid compound of formula (I), a salt of the invention. The salt of the invention may be any stereoisomeric combination of the acid and free base. As used herein, the term "acid" refers to citrate or tartrate, while the term "free base" or "pyrrolidine compound" refers to the pyrrolidinylaminoacetyl pyrrolidine boronic acid. Citrate is not chiral, but tartrate is, and tartrate includes, for example, L-tartrate, D-tartrate, meso-tartrate, as well as a stereomixture such as a racemic mixture, a diastereoisomeric mixture, a mixture of an enantiomeric pair and a diastereomer or an optically-active mixture of at least two stereoisomers. The pyrrolidine compound can be a linear or cyclic form having the structure of formula (I) or (V), respectively. The preferred pyrrolidine compound can be (2R)-1-{7-[(9R)-pyrrolidin-9-ylamino]-acetyl}-pyrrolidine-2-boronic acid or (2R)-1-{7-[(9S)-pyrrolidin-9-ylamino]-acetyl}-pyrrolidine-2-boronic acid. Thus, a preferred salt of the invention includes the citrate or tartrate salt of (2R)-1-{7-[(9R)-pyrrolidin-9-ylamino]-acetyl}-pyrrolidine-2-boronic acid or (2R)-1-{7-[(9S)-pyrrolidin-9-ylamino]-acetyl}-pyrrolidine-2-boronic acid. More specifically, the preferred salt of the invention is the L-tartrate salt of (2R)-1-{7-[(9R)-pyrrolidin-9-ylamino]-acetyl}-pyrrolidine-2-boronic acid, that is, an L-tartrate salt of structure (IA):

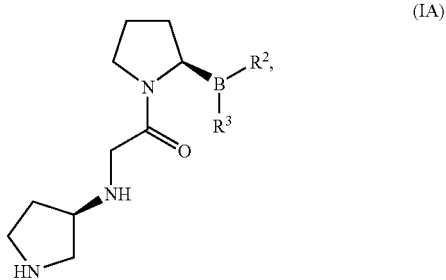

(IA)

wherein $R^2$ and $R^3$ are both hydroxyl groups.

A salt of the invention exhibits improved physical properties that enable the ready isolation of solids and subsequent formulation into a solid dosage form. In contrast, the corresponding free bases were found to deliquesce under ambient conditions. It was also found that many of the salts evaluated (see Table 1) either did not readily form a solid, or, if a solid was formed, deliquesced or became a gummy, intractable material at ambient conditions.

Surprisingly, two organic acid salts, the tartrate and citrate salts of the free base, were found not to display the same physical and chemical instability as the other salts. The salts of the invention, e.g. the preferred mono (2R,3R)-tartaric acid (L-tartaric acid) salt of 1-{7-[(9R)-pyrrolidin-9-ylamino]acetyl}-pyrrolidine-2-boronic acid, readily formed solids and were found not to deliquesce under ambient conditions. Salts of the invention exhibited improved physical stability, such as physical stability under conditions of high temperature and humidity.

Referring to Table 5, below, it can be seen that samples of the L-tartrate salt of (2R)-1-{7-[(9R)-pyrrolidin-9-ylamino]-acetyl}-pyrrolidine-2-boronic acid could be stored for prolonged periods of reasonably high relative humidity (RH); for example storage for 6 months at 75% RH, and storage for 12 months at 60% RH, both at 25° C., were observed to cause no detectable decomposition within statistical error.

A hydrated form of the inventive tartrate or citrate salt can be used in preparation of dosage forms. To prepare these forms, the inventive salt is allowed to equilibrate under ambient conditions to provide a hydrate. The amount of absorbed water in the hydrate can be determined and appropriate allowance is made for the weight of the water in any subsequent preparation, enabling accurate measurement of the desired dosage of the salt. The atmospheric conditions under which pharmaceutical dosage forms are prepared are appropriately controlled to ensure precise and reproducible amounts of the active compound are metered during the manufacturing process. Once the dosage forms are prepared, exposure to variations of humidity will not affect the delivery of the desired dose of the salt even though the actual total weight of individual solid dosage form can vary due to the subsequent absorption or desorption of water. For instance, Example 5 and Table 3 below illustrate management of accurate formulation preparation as a function of water absorption.

The invention includes the citrate and tartrate salt of all of the stereoisomers of a pyrrolidine compound of formula (I), including enantiomers, diastereomers, as well as the racemates and stereoisomeric mixtures. The mixtures may or may not be optically active. In some embodiments, the salt of the invention may have an optical purity of at least about 55%, preferably 80%, more preferably 90%, most preferably 98%. In other embodiments, the salt is an optically-enriched enantiomer of tartrate and/or the pyrrolidine compound. In still other embodiments, the salt is a mixture of stereoisomers including but not limited to unequal mixtures of enantiomers and/or mixtures of diastereomers of the tartrate and/or pyrrolidine compound.

Methods of Treatment

An embodiment of the invention provides a method of inhibition of dipeptidyl peptidase-IV comprising contacting the enzyme, dipeptidyl peptidase-IV, with a salt of the invention in any of its forms as described above. The contact may be accomplished in vitro such as through a diagnostic test or a screening test, or in vivo through an appropriate administrative route as discussed below.

The in vivo methods according to the invention involve a salt of the invention in its role as a selective inhibitor of DPP-IV. For example, the invention provides a method of treatment of a mammal (such as a human) suffering from a malcondition that can be regulated or normalized via inhibition of DPP-IV. The methods of the invention are accomplished by administering to the mammal (e.g., a human) an effective amount of a salt of the invention to treat, control, ameliorate or prevent the malcondition. Treatment is effected through inhibition of DPP-IV. Administration is typically accomplished through use of a pharmaceutical composition containing a salt of the invention. For in vivo use as a DPP-IV inhibitor, a salt of the invention may be formulated in any manner as described herein.

Malconditions that can be treated using a salt of the invention are those that can be regulated or normalized by inhibition of DPP-IV. These malconditions are known to be the result, at least in part, of the reduced presence or absence, or altered activity, of peptides regulated by the enzyme DPP-IV, especially in the context of its physiological role in glycemic control. Thus, these malconditions include those characterized by impaired glycemic control such as Diabetes Mellitus and related conditions. For example, the malcondition can be Type 1 diabetes, Type 2 diabetes, gestational diabetes, MODY, impaired glucose tolerance, impaired fasting glucose, hyperglycemia, impaired glucose metabolism, impaired glucose tolerance (IGT) and its progression to Type II diabetes, hyperinsulinemia, obesity, beta cell degeneration (in particular apoptosis of beta cells), the progression of non-insulin-requiring Type II diabetes to insulin requiring Type II diabetes; loss of the number and/or the size of beta cells in a mammalian subject, and diabetic complications such as retinopathy, neuropathy, nephropathy, cardiomyopathy, dermopathy, diabetes related infection, atherosclerosis, coronary artery disease, stroke and similar malconditions.

In other embodiments of method of treatment according to the invention, insulin resistance is a component of the malcondition that can be regulated or normalized by inhibition of DPP-IV. For example, the malconditions can be impaired fasting glucose, impaired glucose tolerance, polycystic ovarian syndrome and the like. In yet other embodiments, the malcondition that can be regulated or normalized by inhibition of DPP-IV involves a decrease of islet neogenesis, β-cell survival, or insulin biosynthesis.

A salt of the invention may be administered to a mammal, especially a human in need of such treatment, prevention, elimination, alleviation or amelioration of the various malconditions mentioned above. Such mammals include, without limitation, domestic animals such as household pets and farm animals, as well as non-domestic animals such as wildlife.

The amount of salt to be administered to the patient may be any amount appropriate to inhibit DPP-IV that results in treatment of the condition and a beneficial effect for the patient. The amount of the salt to be administered may be an effective dose or an appropriate fraction thereof. Such amounts will depend on individual patient parameters including age, physical condition, size, weight, the condition being treated, the severity of the condition, and any concurrent treatment. Factors that determine appropriate dosages are well known to those of ordinary skill in the art and may be addressed with routine experimentation, using the skill and training of the prescribing physician. For example, determination of the pharmacokinetic and pharmacodynamic properties may be made using standard chemical and biological assays and through the use of mathematical modeling techniques known in the pharmacological arts. The therapeutic utility and dosing regimen may be extrapolated from the results of such techniques and through the use of appropriate pharmacokinetic and/or pharmacodynamic models.

The administered dose of a pyrrolidine compound of the invention may be adjusted according to age, weight and condition of the patient, as well as the route of administration, dosage form and regimen and the desired result. The ultimate choice of dosage, route and pharmaceutical formulation may be determined by the patient's attending physician, whose wisdom and judgment will guide this process. However, a patient may insist upon a lower dose or more tolerable dose for medical reasons, psychological reasons or for virtually any other reasons.

Preferably, the salt of the invention may be administered at a dose of from 0.1 to 30 mg of the salt per kg weight of the mammal, more preferably 2 to 15 mg/kg weight of the mammal. The dose range for adult humans is generally from about 0.5 to about 2,400 mg/day, preferably about 10 mg to about 1,050 mg/day, and more preferably about 50 mg to about 750 mg/day. This may be administered in a single dose or in the form of multiple doses given up to 4 times per day. These doses are based upon weight of the free base alone. Correction for weight contribution by the tartrate or citrate component and the water of hydration would be made to account for actual weight of the hydrated form of the salt to be administered. In some cases, it may be useful to begin with a higher dosage and when the condition is under control to reduce the dosage. Thus, it may be advantageous to administer an initial dose of about 70 mg to about 2,400 mg the first day then a lower dose of about 20 to about 1,200 mg on subsequent days. In other cases, it may be useful to initiate the therapy at a lower dose and increase the dosage if necessary. The exact dosage will depend upon the mode of administration, on the therapy desired, form in which administered, the subject to be treated and the body weight of the subject to be treated, and the preference and experience of the physician or veterinarian in charge. Dosage is described in terms of the free base and is adjusted accordingly for the citrate or tartrate salt.

The use of a salt of the invention also includes the manufacture of a medicine and a method of treatment using such a medicine in the form of a pharmaceutical combination and/or a pharmaceutical composition.

Pharmaceutical Combinations and Their Use in Treatment

A salt of the invention may be combined with a second medicament to form a pharmaceutical combination of the invention. The second medicament is a known agent for treating, controlling, or preventing a malcondition that may be regulated or normalized via inhibition of DPP-IV. The malconditions treated by such combinations are those that may be regulated or normalized via inhibition of DPP-IV.

The second medicament may also include a therapeutically effective amount of a medicament known as an anti-diabetic agent including but not limited to an agent that increases insulin secretion, an agent that increases insulin sensitivity, an agent that reduces the uptake of sugar from the gastrointestinal track, an agent that enhances the effect of endogenous peptides or proteins that play a role in glycemic control, or an agent that acts a replacement therapy for endogenous peptides or proteins that have a known role in glycemic control. Such agents include but are not limited to glyburide (e.g.Micronase and Diabeta), glipizide (e.g. Glucotrol), nateglinide (e.g. Starlix), repaglinide (e.g. Prandin), metformin (e.g. Glucophage), rosiglitazone (e.g. Avandia), acarbose (e.g. Precose), miglitol (e.g. Glyset), exenatide (e.g. Byetta), and insulin (e.g. Humulin and Novolin). Additional exemplary agents include but are not limited to biguanides, chlorpropamide, a glucagon-like peptide-1 (GLP-1) or mimetic thereof such as LY315902 or LY307161, glimepiride, meglitinide, phenformin, pioglitazone, sulfonyl ureas, troglitazone, GI-262570, isaglitazone, JTT-501, NN-2344, L895645, YM-440, R-119702, AJ9677, KAD1129, APR-HO39242, GW-409544, KRP297, AC2993, Exendin-4, and NN2211. The chemical structures, trivial names and pharmacological studies of the foregoing compounds designated by letters and numbers are readily available from the web, for example, by entering the letter/number designation as a search term in the GOOGLE search web site.

A salt of the invention may be used in combination with one or more second medicaments useful as antidiabetic agents (employed to treat diabetes and related diseases). The second medicament may be administered orally in the same dosage with the salt of the invention, or in a separate oral dosage form. The salt of the invention and the second medicament may also be administered, for example by injection, separately, simultaneously or as a mixture.

The pharmaceutical combination of the invention may be formulated as a pharmaceutical composition of a pharmaceutically acceptable carrier along with a salt of the invention and one or more second medicaments.

In the pharmaceutical combination of the invention, the salt of the invention is typically present in a weight ratio to the second medicament of from about 0.01:1 to about 200:1, depending on the identity of the second medicament.

The use of a salt of the invention in combination with one or more other antidiabetic agents can produce antihyperglycemic results greater than that possible from each of these antidiabetic agents alone. The use of a salt of the invention in combination with one or more other antidiabetic agents can also produce a synergistic effect in that the antihyperglycemic result may be greater than the combined additive antihyperglycemic effects produced by these antidiabetic agents.

The effective amount of a second medicament formulated as a component of the pharrmaceutical combination of the invention will follow the recommendations of the second medicament manufacturer, the judgment of the attending physician and will be guided by the protocols and administrative factors for amounts and dosing as indicated in the PHYSICIAN'S DESK REFERENCE (PDR).

The administered dose of a salt of the invention within the pharmaceutical combination will be carefully adjusted according to age, weight and condition of the patient, as well as the route of administration, dosage form and regimen and the desired result. The ultimate choice of dosage, route and pharmaceutical formulation will determined by the patient's attending physician, whose wisdom and judgment will guide this process.

The compositions described above may be administered in the dosage forms as described above in single or divided doses of one to four times daily. It may be advisable to start a patient on a low dose combination and work up gradually to a high dose combination.

Pharmaceutical Compositions of the Invention

The invention includes a pharmaceutical composition containing a salt of the invention, with or without another medicament as described above, in association with a pharmaceutical carrier. The pharmaceutical composition may be formulated with one or more carriers such as conventional solid or liquid vehicles or diluents and pharmaceutical additives of a type appropriate to the mode of desired administration. A salt of the invention in a pharmaceutical composition may be administered to mammalian species, especially humans, by an oral, buccal, rectal, pulmonary or similar route, for example, in the form of tablets, capsules, granules or powders. It may be administered by a parenteral route in the form of injectable preparations. It may be administered by a transdermal route either by a release patch for transdermal delivery or by electro-transport using an appropriate delivery device.

A pharmaceutical composition containing a salt of the invention may be prepared by conventional techniques, e.g. as described in Remington: The Science and Practice of Pharmacy, 19$^{th}$ Ed., 1995. The composition may appear in a conventional form, for example, capsule, tablet, aerosol, solution, suspension or in a form suitable for topical application.

A typical pharmaceutical composition includes a salt of the invention formulated with a pharmaceutically acceptable carrier which may be an excipient or a diluent, or may be enclosed within a carrier which can be in the form of a liquid, capsule, sachet, tablet, paper or other container. In making the composition, conventional techniques for the preparation of pharmaceutical compositions may be used.

For example, a salt of the invention may be mixed with a carrier, or diluted by a carrier, or enclosed within a carrier, which may be in the form of an ampoule, capsule, tablet, sachet, paper, or other container. When the carrier serves as a diluent, it may be solid, semi-solid, or liquid material that acts as a vehicle, excipient, or medium for the active compound. The salt may be adsorbed on a granular solid container for example in a sachet. Some examples of suitable carriers include, without limitation, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax.

A formulation may be mixed with auxiliary agents which do not deleteriously react with the pyrrolidine compound. Such additives may include, without limitation, wetting agents, emulsifying and suspending agents, salt for influencing osmotic pressure, buffers and/or coloring substances preserving agents, sweetening agents or flavoring agents. A pharmaceutical composition can also be sterilized if desired.

The route of administration may be any route that effectively transports the salt of the invention to the appropriate or desired site of action, such as oral, nasal, pulmonary, buccal, rectal, subdermal, intradermal, transdermal or depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form, or it may be in the form of a troche or lozenge. If a liquid carrier is used, the preparation may be in the form of a syrup, emulsion, soft gelatin capsule or sterile injectable liquid such as an aqueous or non-aqueous liquid suspension or solution.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, a pharmaceutical composition may be a powder suitable for reconstitution with an appropriate solution as described above. Examples of these include, but are not limited to, freeze dried, rotary dried or spray dried powders, amorphous powders, granules, precipitates, or particulates. For injection, a pharmaceutical composition may optionally contain stabilizers, pH modifiers, surfactants, bioavailability modifiers and combinations of these. A salt of the invention may be formulated for parenteral administration by injection such as by bolus injection or continuous infusion. A unit dosage form for injection may be in ampoules or in multi-dose containers.

A pharmaceutical composition of the invention may be designed to provide quick, sustained, or delayed release of the active ingredient after administration to the patient by employing procedures well known in the art. Thus, a pharmaceutical composition may also be formulated for controlled release or' for slow release.

A pharmaceutical composition of the invention may include, for example, micelles or liposomes, or some other encapsulated form, or may be administered in an extended release form or an enteric coated form to provide a prolonged storage and/or delivery effect. Therefore, the pharmaceutical composition may be compressed into pellets or cylinders and implanted intramuscularly or subcutaneously as depot injections or as implants such as stents. Such implants may employ known inert materials such as silicones and biodegradable polymers, e.g., polylactide-polyglycolide. Examples of other biodegradable polymers include poly (orthoesters) and poly (anhydrides).

A salt of the invention may be formulated as a sustained release implant or implantable material suitable for continuous administration over a significant period of time. Typical sustained release implants are formed from polymers of pharmaceutically acceptable, biodegradable polymers such as polymers and copolymers of lactic acid, lactide, glycolic acid, glycolide, caproic acid and caprolactone. The dose and amount of a salt of the invention within the implant will be calculated to deliver the desired single dose blood level of the salt.

For nasal administration, a pharmaceutical composition may contain a salt of the invention dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with a salt of the invention dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet may be prepared by conventional tabletting techniques as follows.

A typical tablet having an equivalent 400 mg free base strength may be prepared by formulating 650 mg of the L-tartrate salt, 215 mg of microcrystalline cellulose, 50 mg of dibasic calcium phosphate, 20 mg of copolyvidone, 50 mg of crospovidone, 10 mg of colloidal silicon dioxide, 5 mg of magnesium stearate and 3% solid opadry AMB. Another typical tablet composition having an equivalent 50 mg free base strength may be formulated by combining 80 mg of the L-tartrate salt, 815 mg of microcrystalline cellulose, 50 mg of dibasic calcium phosphate, 20 mg of copolyvidone, 20 mg of crospovidone, 10 mg of colloidal silicon dioxide, 5 mg of magnesium stearate and 3% solids opadry AMB. The salt can be subjected to milling and screening through a 20 mesh screen. The milled and screened salt can be blended with microcrystalline cellulose, copolyvidone, crospovidone and colloidal silicon dioxide in a suitable V-shell blender for an appropriate time and rpm. The resulting composition can be mixed with the lubricant magnesium stearate. Tablets can be compressed using the lubricated blend at a theoretical tablet weight of 1000 mg. Part of compressed tablets can be coated using Opadry AMB. Coating can be continued until an appropriate solid weight gain is achieved.

A further typical capsule for oral administration contains a salt of the invention (200 mg of free base equivalent), lactose (75 mg) and magnesium stearate (15 mg). The mixture is passed through a 60 mesh sieve and packed into a No. 1 gelatin capsule.

A typical injectable preparation is produced by aseptically placing a salt of the invention (at 200 mg of free base equivalent) into a vial, aseptically freeze-drying and sealing. For use, the contents of the vial are mixed with 2 mL of physiological saline, to produce an injectable preparation.

A salt of the invention may be dispensed in unit dosage form from about 0.5 to about 2000 mg of active ingredient together with a pharmaceutically acceptable carrier per unit dosage. Usually, a dosage form suitable for oral, nasal, pulmonary or transdermal administration includes from about 0.5 mg to about 2000 mg, preferably from about 10 mg to about 1000 mg per day, more preferably from about 50 mg to about 750 mg, of a salt (as measured by the free base equivalent) admixed with a pharmaceutically acceptable carrier or diluent.

The drug release properties of tablets made according to the invention indicated appropriate delivery of the pyrrolidine compound. Samples of the tablets were tested for flow, hardness, disintegration and drug release. In particular, adequate flow was estimated by Carr's Index and visual observation on lubricated blends. Compressed tablets had acceptable hardness of about 12 kP. Tablets also had acceptable disintegration time (less than 15 minutes). Data without controlled comparison showed adequate in vitro release (more than 90% in 30 minutes).

When preparing a pharmaceutical formulation containing a salt of the invention, the physical property of the salt should be taken into account.

For example, the L-tartrate salt remained a processable solid for several days at ambient temperature and a relative humidity of 75%. It also has improved chemical stability relative to the free base at 25° C./60% RH, 40° C./75% RH and 60° C/ambient humidity, and remained a processable solid at 63% relative humidity and room temperature for two months. Thus, the appropriate temperature and relative humidity should be selected and maintained during preparation of pharmaceutical formulations containing a salt of the invention. If ambient temperature is selected, for example, a salt of the invention can be maintained at moderate humidity, that is below 65% relative humidity, or preferably, below 60% relative humidity.

In addition, although a salt of the invention is physically stable in ambient conditions, its hygroscopicity should be taken into account. Thus, when preparing a pharmaceutical formulation containing a salt of the invention, hygroscopically stable forms of the salt should be used. A salt of the invention is hygroscopically stable when its weight is stable under an appropriate temperature and relative humidity. Thus, prior to metering, a salt of the invention should be equilibrated to the appropriate temperature and humidity.

Furthermore, when weighing or otherwise metering a salt of the invention in the preparation of pharmaceutical compositions, the amount of water absorbed should be taken into account. For example, to achieve an appropriate effective dose, the salt of the invention, equilibrated to the selected temperature and humidity, can be prepared and the weights of water of hydration measured. The water measurement and consequent weight correlation will provide the actual amount of salt for a selected effective dose.

If a disintegrant is included in the formulation of a tablet or capsule, then the formulation should be designed and prepared in such a way so as to avoid untimely breakup and disintegration of the tablet or capsule resulting from reaction of the disintegrant with the water absorbed by the salt.

A pharmaceutical combination of the invention may be formulated as a pharmaceutical composition employing all of the embodiments, carriers, route designs and the like described above for formulation of a pharmaceutical composition of a salt alone.

The invention also encompasses prodrugs of a salt of the invention which on administration undergo chemical conversion by metabolic processes before becoming active pharmacological substances. In general, such prodrugs will be functional derivatives of a salt of the invention which are readily convertible in vivo into a salt of the invention. Conventional procedures for the selection and preparation of suitable prodrug derivatives are described, for example, in "Design of Prodrugs", ed. H. Bundgaard, Elsevier, 1985.

Thus, another aspect of the invention provides a pharmaceutical composition of a salt of the invention, alone or in combination with another type antidiabetic agent and/or other type therapeutic agent.

Additional embodiments of the invention are represented by: (1) a pharmaceutical composition including a salt of the invention, as described above, together with at least one pharmaceutically acceptable carrier or diluent; (2) methods of making a pharmaceutical composition of a salt of the invention wherein the pharmaceutically acceptable carrier or diluent is suitable for oral administration; (3) methods of making a pharmaceutical composition ofa salt of the invention suitable for oral administration further including the step of formulating the composition into a tablet or capsule; (4) methods of making a pharmaceutical composition of a salt of the invention wherein the pharmaceutically acceptable carrier or diluent is suitable for parenteral administration; (5) methods of making a pharmaceutical composition of a salt of the invention suitable for parenteral administration further including the step of lyophilizing the composition to form a lyophilized preparation.

DPP-IV inhibitory activity of a salt of the invention may be determined by use of an in vitro assay system. Inhibition constants ($K_i$ or $IC_{50}$ values) for the DPP-IV inhibitors of the invention may be determined by the method described below.

Methods of Preparing a Salt of the Invention

An embodiment of the invention also provides a process for preparing a salt of the invention. Preparation of the free base pyrrolidine compound is provided in U.S. patent application Ser. No. 60/704,380, filed Aug. 1, 2005, and in U.S. patent application Ser. No. 10/514,575, filed Nov. 15, 2004. A general synthetic scheme for preparation of a tartrate salt of the invention is shown below as Scheme 1.

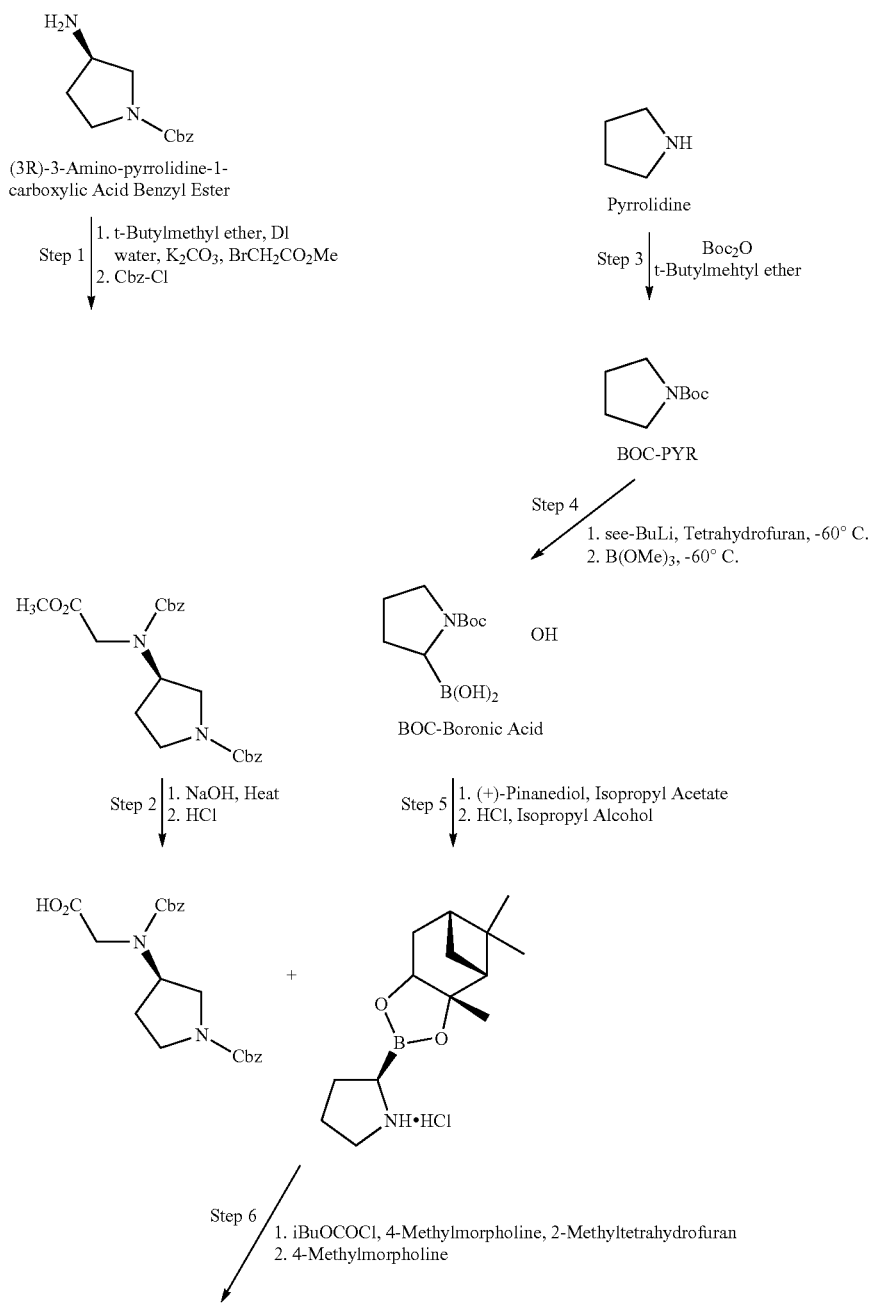

Scheme 1

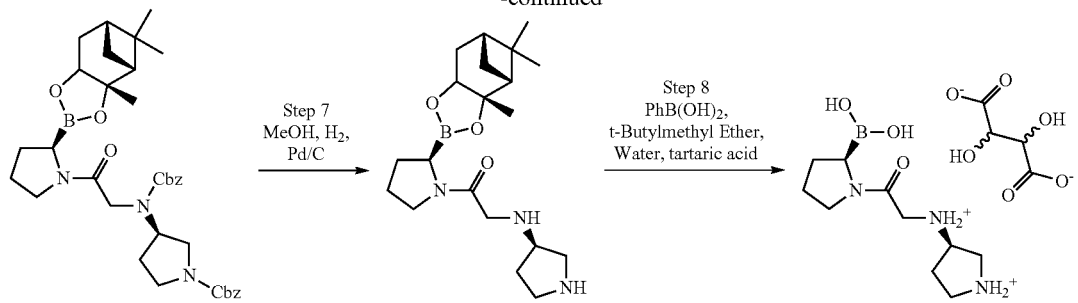

The salt of the invention may be obtained as the direct product of compound synthesis as illustrated in the synthetic scheme above (see step 8) and described in detailed in Example 4 below. In the alternative, the free base may be dissolved in a suitable solvent, and then the salt can be isolated by evaporating the solvent. A suitable solvent can be, for example, a hydroxylic organic solvent or a polar aprotic organic solvent, or water. The solvent can be evaporated in numerous ways including, without limitation, by spray drying or freeze drying, or otherwise separating the salt and solvent, e.g. by precipitation. Thus, an example of a method for preparing a salt of the invention include, without limitation, dissolving the free base in an alkanol of 1 to 6 carbons that contains an appropriate amount of an appropriate acid, e.g. a stoichiometric amount of citrate or tartrate, and then the salt may be isolated by evaporating the solvent. Alternatively, the acid may be added to a solution of the free base, and then a salt is isolated by removal of the solvent. In addition, the processes for forming a pharmaceutically acceptable salt from an amine compound such as a pyrrolidine compound of the invention are well-known in the art. See, for example, "The Practice of Medicinal Chemistry, Second Edition", by Camille G. Wermuth, Academic Press, New York, N.Y., 1996.

The invention will be further described in the following examples, which do not limit the scope of the invention described in the claims.

EXAMPLES

The preparation and biological activity of the free base are described in U.S. patent application Ser. No. 11/381,085, filed May 1, 2006, which is herein incorporated by reference.

Example 1

Salt Preparation

The following procedure was used to prepare or in attempts to prepare various salts of the pyrrolidine compound of formula I (see FIG. 1). To a 1 L flask under a nitrogen blanket, 50 mmol of the free base compound was added, and then 250 mL of isopropyl alcohol (IPA) was added. The mixture was stirred for 20-30 minutes to fully dissolve the solid. To a second 500 mL flask under a nitrogen blanket, 50 mmol of the desired acid (tartaric or citric acid) was added, and then 250 mL of IPA was added. The mixture was warmed gently to 30° C. and stirred for 10-20 minutes until the solid dissolved. The acid solution was added rapidly to the free-base solution, and the mixture was stirred at room temperature for 0.5 hours before filtration. Any resulting cake was air dried for 0.5 hours and then washed with 150 mL of methyl tertiary-butyl ether (MTBE), air dried for 1-2 hours, and then dried in a vacuum oven at 40-50° C. for an overnight period.

Attempts were made to create the acetate, adipate, 10-camphor sulfonate, citrate, decanoate, hydrobromate, L-ascorbate, L-glutamate, L-lactate, L- and R-tartrate, 2-naphthalene sulfonate, palmitate, and succinate salt of the pyrrolidine compound. Results are summarized in Table 1 below.

TABLE 1

| Acid | Molecular Weight | Reference TWD-005- | % Yield | Comments |
| --- | --- | --- | --- | --- |
| Succinic Acid | 118.1 | 150 | NA | Solids obtained but liquefied on filtration |
| Adipic Acid | 146.14 | 150 | NA | No solids; diluted with MTBE; gave solids/liquefied |
| 2-Naphthalene Sulfonic Acid | 208.24 | 150 | NA | Gave solids; liquefied on filtration |
| L-Tartaric Acid | 150.09 | 154 | 95.5 | Good filterable solid |
| D-Tartaric Acid | 150.09 | 170 | 90.0 | Good filterable solid |
| D,L-Tartaric Acid | 150.09 | 168 | 85.4 | MeOH needed for solubility; Good filterable solid |
| Citric Acid | 192.12 | 154 | 100 | Good filterable solid |
| Palmitic Acid | 256.4 | 156 | NA | No solids; gummy solids with MTBE |
| Decanoic Acid | 172.27 | 156 | NA | No solids; gummy solids with MTBE |
| L-Ascorbic Acid | 176.12 | 158 | NA | Solids obtained but liquefied on filtration |
| L-Lactic Acid | 90.08 | 158 | NA | No solids; No solids with MTBE |
| 10-Camphor Sulfonic Acid | 232.3 | 158 | NA | No solids; No solids with MTBE |
| Acetic Acid | 60.05 | 158 | NA | No solids; No solids with MTBE |
| L-Glutamic acid | 147.13 | 158 | NA | Acid insoluble in everything; also no solids obtained using water |
| Hydrobromic Acid | 80.92 | 158 | NA | Gave solids; liquefied on filtration |

Only citrate and the L-, D-, and DL-tartrate salts could be isolated. The other salts either yielded no solids or yielded solids that liquefied on filtration. All salts were amorphous by differential scanning calorimetry (DSC). The citrate and the D-tartrate salts were not stable when submitted to 75% relative humidity (RH) but were stable at 63% RH. In contrast, the L-tartrate salt was stable when submitted to 75% RH. For the L-tartrate salt, a total of 18.12 g of a cream colored solid was obtained, 92.6% of theory.

Figure 2:
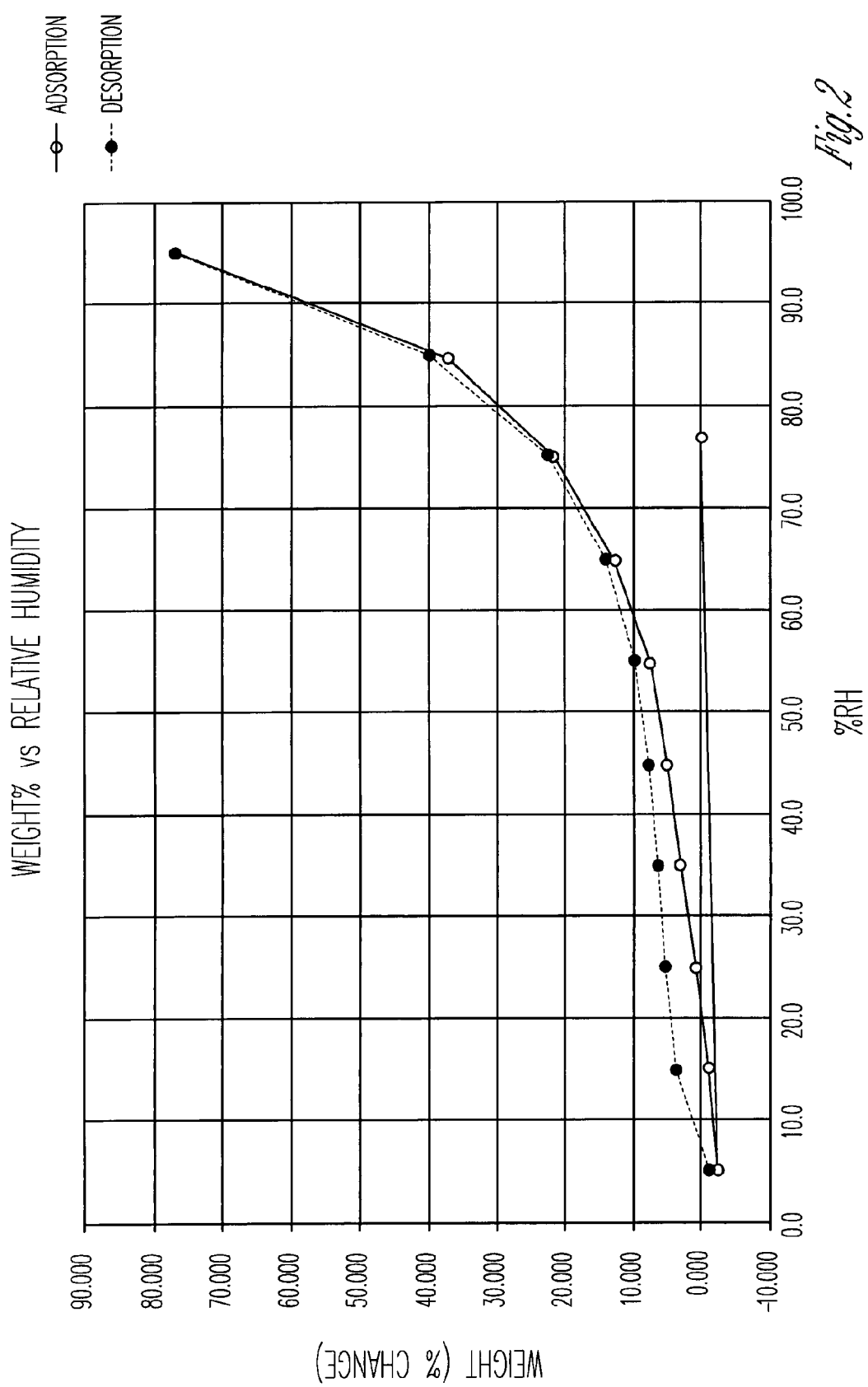
FIG. 2 is a graph illustrating the humidity absorption of the L-tartrate salt of (2R)-1-{7-[(9R)-pyrrolidin-9-ylamino]-acetyl}-pyrrolidine-2-boronic acid with increasing relative humidity.
Figure 3:
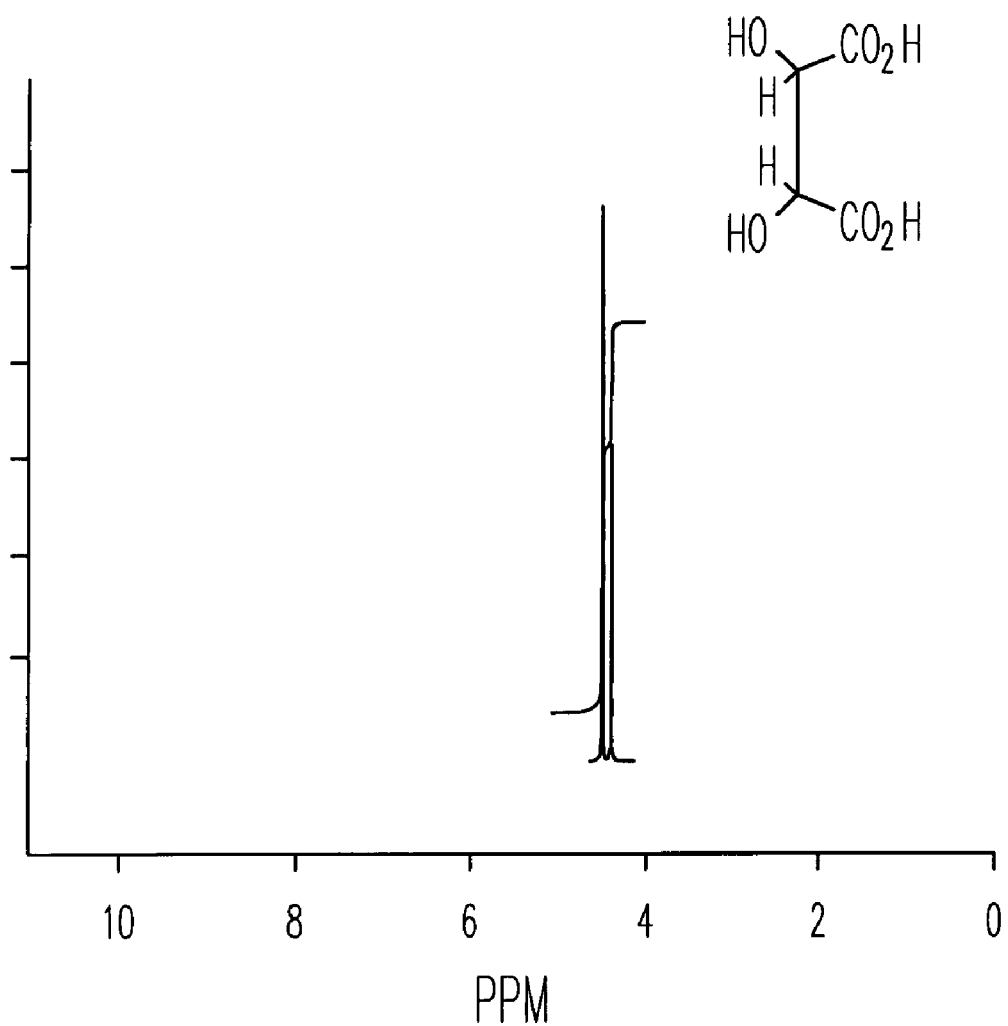
FIG. 3 is a chromatogram obtained from high performance liquid chromatography (HPLC) analysis of L-tartrate.
Figure 4:
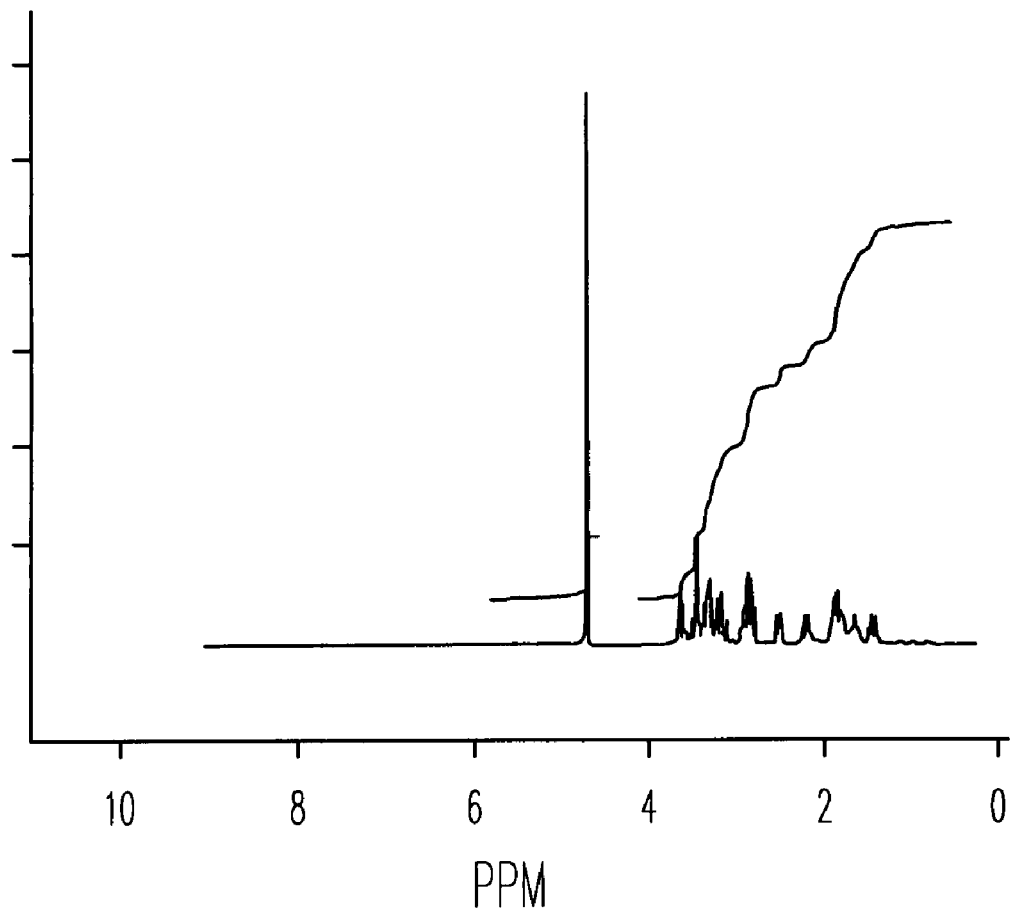
FIG. 4 is a chromatogram obtained from HPLC analysis of the pyrrolidine compound.
Figure 5:
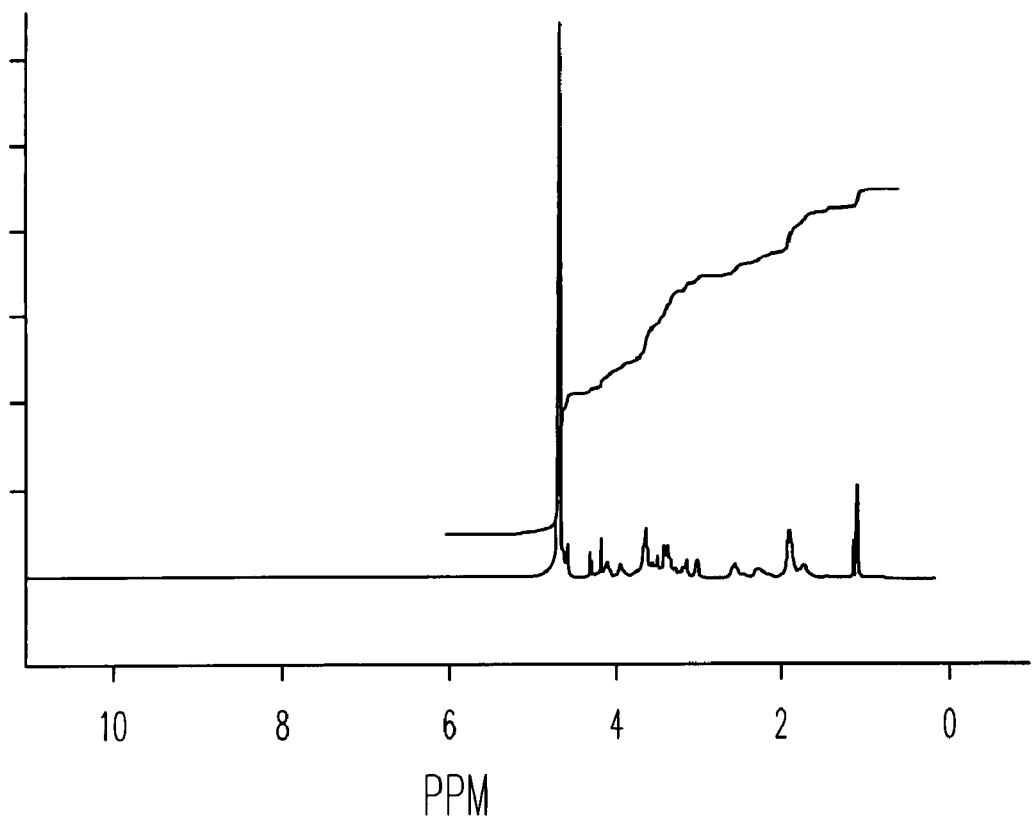
FIG. 5 is a chromatogram obtained from HPLC analysis of the L-tartrate salt of the pyrrolidine compound.
Figure 6:
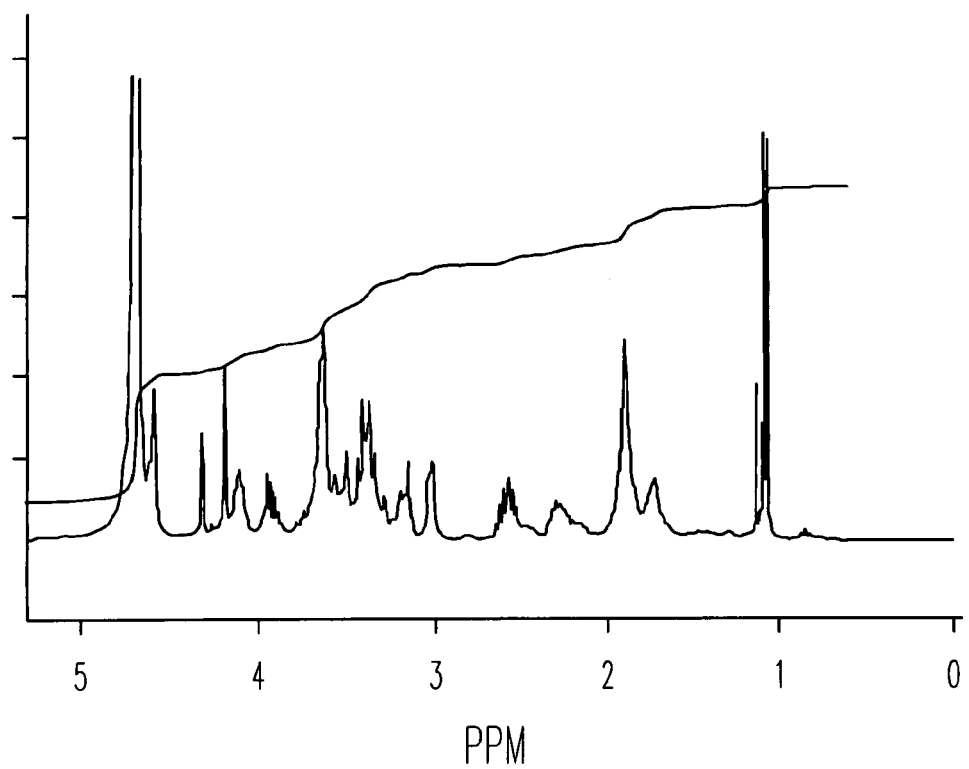
FIG. 6 is a magnification of the peaks corresponding to the L-tartrate salt of the pyrrolidine compound.

The L-tartrate salt of (2R)-1-{7-[(9R)-pyrrolidin-9-ylamino]-acetyl}-pyrrolidine-2-boronic acid has the molecular formula $C_{10}H_{20}BN_3O_3$—$C_4H_4O_6$ and a molecular weight of 391.25 g/mole. It is a white to pale tan amorphous solid that is freely soluble in water and alcohols (>2000 mg/mL). It is moderately hygroscopic and remains a processable solid at ambient conditions. The water sorption of the tartrate salt is illustrated in FIG. 2.

Example 2

Spray Drying Procedure

For spray drying, a laboratory scale spray dryer, SD011 (BUCHI, model B-290 Advanced), equipped with a two fluid nozzle was used. Nozzle cap and diameter were 1.5 and 0.7 mm, respectively. A high-performance cyclone was used to collect the dried product.

The flow of drying nitrogen was controlled by the speed of the fan (F_drying). In these tests, the fan circulated nitrogen at 100% of capacity (flow rate at approximately 35 kg/h). The atomizing nitrogen flow (F-atm), controlled by a needle valve, was set to 357 L/h (30 mm height in the rotameter). Before initiating each test, the dryer was stabilized with deionized water. The solution flow (F-feed) was set to 9 mL/min (30% of the peristaltic feed pump speed). The inlet temperature (T_in) was controlled by an electric heater (HX) and was adjusted in order to obtain the target outlet temperature (T_out) (100° C.). The operational parameters were defined based on one used test previously performed in SD011 for 17DC01 (MAR-001-026).

Products collected from the cyclone and from the bottom of the drying chamber were combined.

Example 3

Preparation of the L-tartrate Salt by Spray Drying

A solution of 1.00 g of the free base compound and 4.06 g of deionized water, and a solution of 0.62 g of L-tartaric acid and 2.44 g of deionized water, were stirred for 15 minutes at 20-25° C. Then the L-tartaric acid solution was added to the solution of free base compound and the mixture was stirred for 15 minutes at 20-25° C. Prior to spray drying, the reaction mixture had a solid content of approximately 25% (w/w). This procedure was scaled up to convert 500 g of the free base to the L-tartrate salt in three batches.

Results for spray dried products from three different reactions are summarized in Table 2.

TABLE 2

| Batch | Purity (% in area by HPLC) | | | Weight (g) | | Yield (%) | |
|---|---|---|---|---|---|---|---|
| | In solution | Cyclone | Chamber | Cyclone | Chamber | Molar | Mass |
| #1 | 93.2 | 93.4 | —* | 141 | —* | 87 | 141 |
| #2 | 94.6 | 94.3 | 93.9 | 243 | 44 | 89 | 144 |
| #3 | 94.3 | 94.3 | 94.7 | 208 | 60 | 83 | 134 |
| Combined | | 93.7 | | 696 | | 86 | 139 |

*Sprayed dried product could be collected in the cyclone (majority) or on bottom of the drying chamber (temperature sensitive products may have lower purity in chamber due to exposure to higher temperature for longer periods of time). In this batch, the amount collected in the chamber was so small that no analysis was done.

In addition, the solutions before spraying and the spray dried product were analyzed for purity by HPLC using the following method. A Waters Symmetry C18 (3.0×150 mm, 3.5 um) column was used. The mobile phase A consisted of 25 mM sodium octanesulfonic Acid, 0.1% TFA in 90:10 water: methanol. The mobile phase B consisted of 25mM sodium octanesulfonic acid, 0.1% TFA in 25:75 water:methanol. Column temperature was 60° C., and the detection wavelength was 210 nm. The injection volume was 15 µL; flow rate was 1.0 mL/minute for a run time of 70 minutes. The gradient was as follows:

| Time (min) | % mobile phase A | % mobile phase B |
|---|---|---|
| 0 | 100 | 0 |
| 5 | 100 | 0 |
| 50 | 45 | 55 |
| 60 | 0 | 100 |
| 65 | 0 | 100 |
| 65.1 | 100 | 0 |
| 70 | 100 | 0 |

Note:
Run column at 0.1 mL/min until column is equilibrated to 60° C.

The resulting chromatograms shown in FIGS. 3 to 6 correspond to that for tartrate, the pyrrolidine compound and the L-tartrate salt, respectively.

Figure 7:
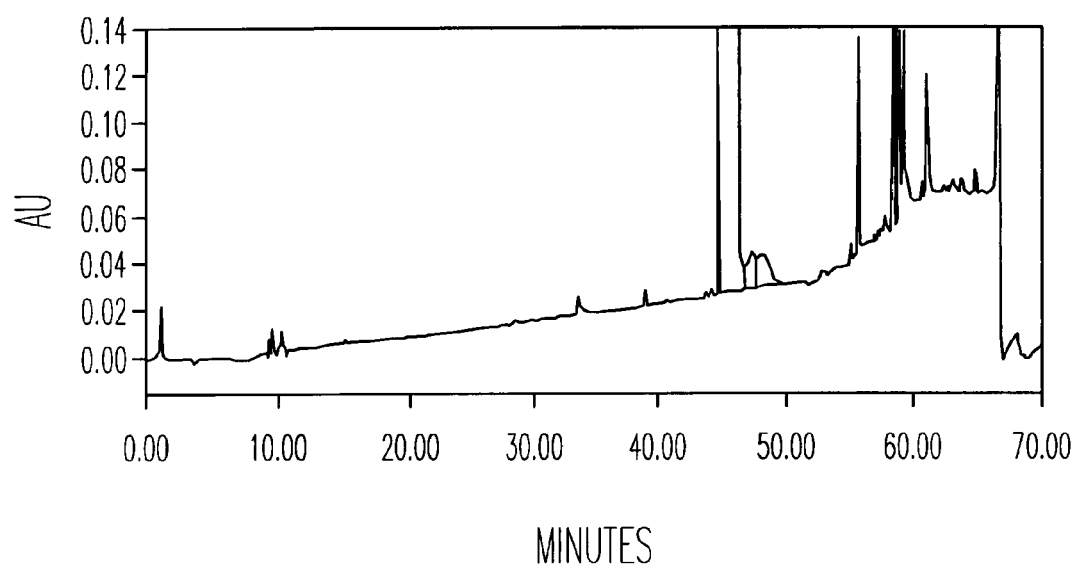
FIG. 7 is a chromatogram obtained from HPLC analysis of the spray dried product showing that the L-tartrate salt of the invention was isolated by spray drying without product degradation.

The spray dried product from the three reaction batches were combined and the chromatogram obtained by HPLC analysis of the combined spray dried product is illustrated in FIG. 7.

In sum, the L-tartrate salt of (2R)-1-{7-[(9R)-pyrrolidin-9-ylamino]-acetyl}-pyrrolidine-2-boronic acid isolated by spray drying had minimal or no product degradation.

Example 4

Preparation of a Tartrate Salt of the Invention as a Direct Product of Compound Synthesis A tartrate salt of the invention was prepared from the protected free base as follows. A reactor was charged 1.0 kg of the protected free base, 0.40 kg of the tartaric acid, and 2.0 kg (2L) of purified water. The mixture was agitated for not less than 1 hour, while the content of the reactor was kept below 30° C. as the initial reaction was sometimes exothermic. Then 0.33 kg of phenyl-boronic acid and 3.7 kg of methyl-tert-butyl-ether (5 L) were added, and the mixture was stirred for not less than 2 hours at 15° C. to 25° C. A sample was collected and analyzed by HPLC. If the reaction mixture had more than 0.5% free base, it was stirred for another 1-3 hour and resampled. If the mixture had 0.5% or less of the free base, then agitation was stopped and the layers allowed to separate for not less than 15 minutes. The organic phase was discarded, and the bottom aqueous phase used in the next step.

The aqueous phase was extracted with 4.3 kg of 2-methyl-tetrahydrofuran (5 L) by agitation for not less than 10 minutes, and then aqueous and organic layers were allowed to separate over not less than 15 minutes. The organic phase was again discarded, and the aqueous phase subjected to two more cycles of extraction with 4.3 kg of 2-methyl-tetrahydrofuran (5 L) as described.

The resulting aqueous phase was reacted with 3.7 kg of methyl-tert-butyl-ether (5 L), and the mixture agitated for not less than 10 minutes. Then the layers were allowed to separate over not less than 15 minutes. Again, the organic phase was discarded, and the bottom aqueous phase collected. A sample was collected for HPLC analysis.

The resulting aqueous phase was polish filtered and a sample analyzed by HPLC. Residual solvents were removed by application of a vacuum at −0.8 to −0.9 bar for 2 hours at 35° C. to 50° C. A sample of the resulting solution was collected for HPLC analysis.

A part of the solution was transferred to freeze dryer trays and frozen. The frozen trays were then removed and placed in the product freezer and held. The remainder of the product solution was loaded into freeze dryer trays and subjected to freeze drying. Then the previously frozen trays were subjected to freeze drying.

Example 5

Properties of the Tartrate Salt

Figure 8:
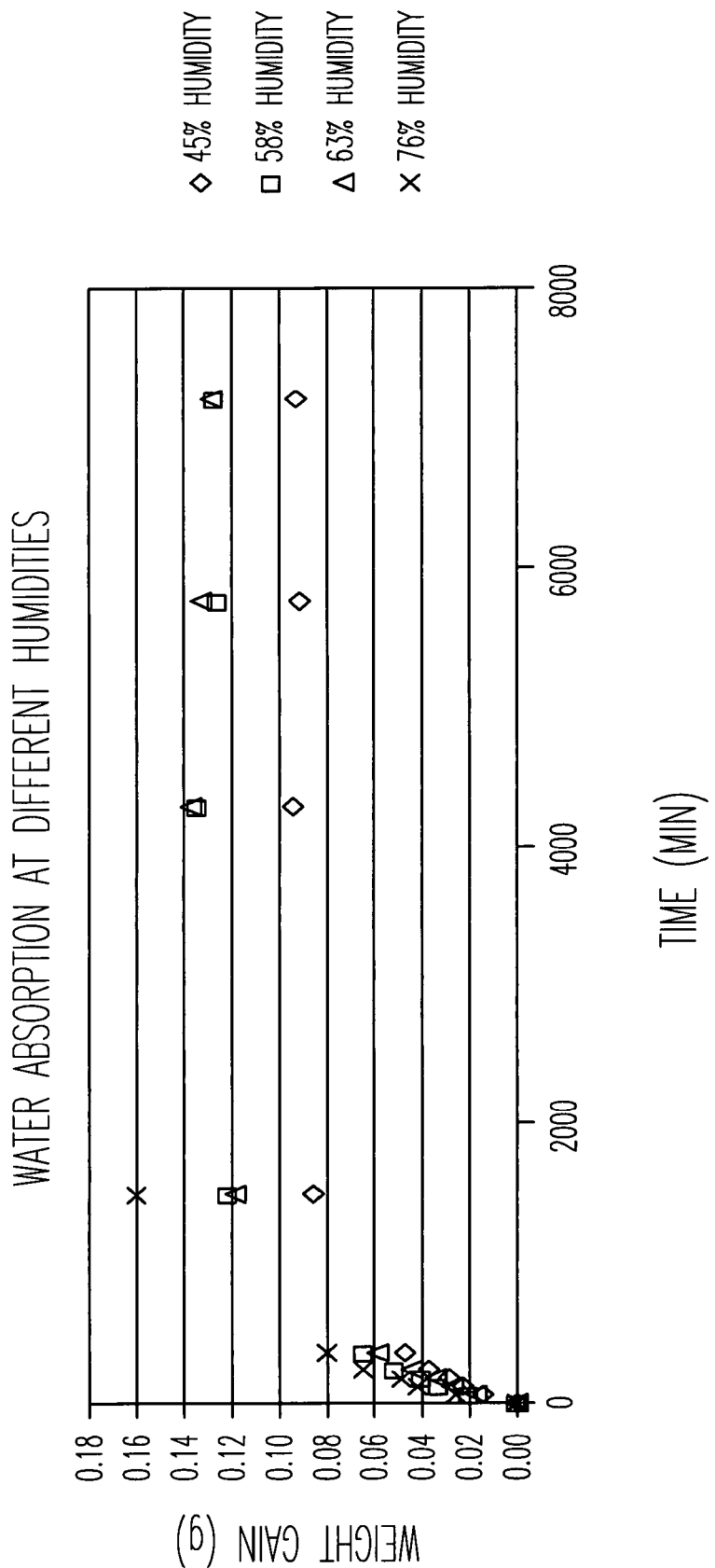
FIG. 8 is a graph illustrating the typical humidity absorption of the tartrate salt of the invention over five days at 45%, 58%, 63% and 76% relative humidity.

Physical Stability in Humidity Chambers. The tartrate salt was prepared on a 50 mmol scale to give 18.12 g of a cream colored solid. Four 1.0 g samples of the salt were placed in four separate humidity chambers at 45%, 58%, 63%, and 76% relative humidity at ambient temperature (68° F. to 72 ° F.). Samples were weighed hourly at first, and then on daily intervals. Results are illustrated in FIG. 8.

After five days, the samples gained between 9% to 13% water at RH of 45% to 63%, with most of the gain occurring within the first three days. The rate of water absorption was proportional to the relative humidity, with little difference between 58% RH and 63% RH. Thus, the tartrate salt was physically stable (i.e., remained a flowable solid) at room temperature and RH up to 63%.

A sample of the tartrate salt was stored in an open container at room temperature and 45% RH for two months. The material maintained good flow properties after two months.

Figure 9:
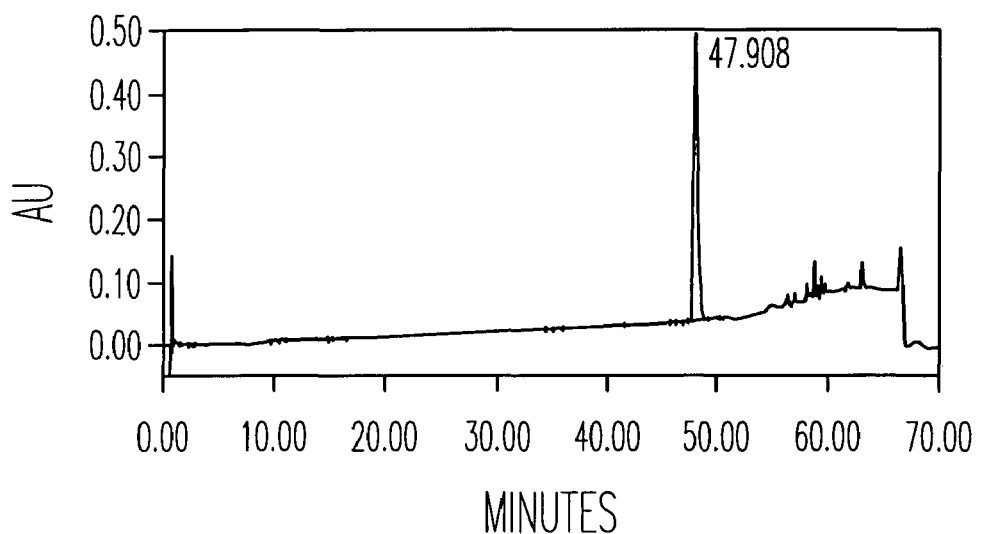
FIG. 9 is a chromatogram obtained from HPLC analysis of the L-tartrate salt of the invention prior to 2 months incubation in a 45% relative humidity chamber.
Figure 10:
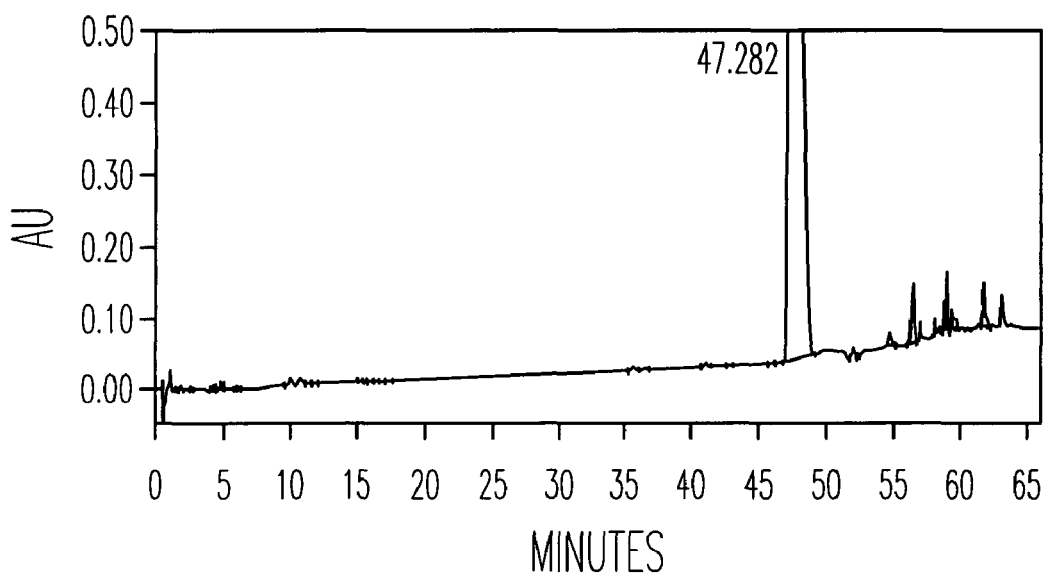
FIG. 10 is a chromatogram obtained from HPLC analysis of the L-tartrate salt of the invention after 2 months incubation in a 45% relative humidity chamber.

Chemical Stability. Chemical stability was determined using HPLC. The L-tartrate salt was held continuously in chamber at 45% RH for two months. FIGS. 9 and 10 are the HPLC chromatograms for salt prior to and after two months at 45% RH. Little or no change in the purity was observed.

The chemical stability of the tartrate salt and the free base was also determined after one and three months at 25° C., 40° C. and 60° C. Results are summarized in the following table.

TABLE 3

| Conditions | Assay (%) | | Total Impurities (%) | |
| --- | --- | --- | --- | --- |
| | Free Base | Tartrate | Free Base | Tartrate |
| Initial | 96 | 99 | 7.6 | 6.5 |
| 3 months at 25° C. | NA | 99 | NA | 5.7 |
| 1 month at 40° C. | 97 | NA | 15.4 | NA |
| 3 months at 40° C. | 50 | 97 | 29.6 | 5.9 |
| 1 month at 60° C. | NA | 100 | NA | 5.8 |
| 3 months at 60° C. | NA | 92 | NA | 7.4 |

Example 6

DPP-VII, DPP-VIII, DPP-IX, and FAP Assays

Analysis of the biological activity and selectivity of the free base is described in U.S. patent application Ser. No. 11/381,085, filed May 1, 2006, which is herein incorporated by reference. The biological activity and selectivity of the tartrate salt was compared with that of the free base using the same method as described in the Ser. No. 10/381,085 application. Results indicate that the free base and the L-tartrate salt have comparable potencies and selectivity against the various DPP tested. Specifically, like the free base, the tartrate salt showed excellent selectivity for DPP-IV relative to DPP-VIII.

Example 7

Tablet Formation

Tablets having 400mg and 50 mg of a salt of the invention were prepared as follows. The salt was milled and screened through a 20 mesh screen and then blended with microcrystalline cellulose, copolyvidone, crospovidone and colloidal silicon dioxide in a suitable V-shell blender for 10 minutes at 25 rpm. The resulting composition was mixed with lubricant magnesium stearate for 2 minutes at 25 rpm. Tablets were compressed using the lubricated blend at a theoretical tablet weight of 1000 mg using 0.785" x 0.370" modified capsule shaped tablet tooling. Parts of compressed tablets were coated using Opadry AMB. Coating was continued until approximately 3% solids weight gain was achieved. Compositions of the tablets are as follows.

TABLE 4

| | Quantity (mg/Tablet) | | |
| --- | --- | --- | --- |
| Ingredient | 400 mg strength | 50 mg strength | Function |
| Salt of the invention | 650 | 80 | Drug substance |
| Microcrystalline cellulose | 215 | 815 | diluent |
| Dibasic calcium phosphate | 50 | 50 | Diluent |
| copolyvidone | 20 | 20 | Binder-moisture barrier |
| Crospovidone | 50 | 20 | Super disintegrant |
| Colloidal silicon dioxide | 10 | 10 | Glidant |
| Magnesium stearate | 5 | 5 | Lubricant |
| Opadry AMB | 3% solids | 3% solids | Moisture Barrier Film Former |

TABLE 5

| 12 Month Stability Study Tartrate Salt | | | | |
| --- | --- | --- | --- | --- |
| Time point | Appearance | Water | Assay (HPLC) | Purity (HPLC) |
| time = 0 T = N/A, RH = N/A | Off white solid | 10.4 | 105.1 | 98.3 |
| time = 1 month T = 5° C., RH = N/A | Off white solid | 9.8 | 105.7 | 98.1 |
| time = 1 month T = 25° C., RH = 60% | Off white solid | 9.9 | 105.7 | 98.1 |
| time = 1 month T = 40° C., RH = 75% | Off white solid | 10.0 | 106.0 | 98.2 |
| time = 3 months T = 5° C., RH = N/A | Off white solid | 9.6 | 106.2 | 98.0 |
| time = 3 months T = 25° C., RH = 60% | Off white solid | 9.4 | 106.7 | 98.1 |
| time = 3 months T = 40° C., RH = 75% | Off white solid | 9.2 | 105.3 | 97.9 |
| time = 6 months T = 5° C., RH = N/A | Off white solid | 8.9 | 104.6 | 97.9 |
| time = 6 months T = 25° C., RH = 60% | Off white solid | 9.3 | 105.9 | 97.9 |

TABLE 5-continued

12 Month Stability Study Tartrate Salt

| Time point | Appearance | Water | Assay (HPLC) | Purity (HPLC) |
|---|---|---|---|---|
| time = 6 months T = 40° C., RH = 75% | Yellowish solid | 9.5 | 105.6 | 97.7 |
| time = 9 months T = 5° C., RH = N/A | Off white solid | 9.1 | 106.7 | 97.8 |
| time = 9 months T = 25° C., RH = 60% | Off white solid | 9.0 | 107.3 | 97.8 |
| time = 12 months T = 5° C., RH = N/A | Off white solid | 9.3 | 107.8 | 98.0 |
| time = 12 months T = 25° C., RH = 60% | Slightly yellow solid | 9.3 | 107.7 | 97.9 |

Table 5 shows the results of a 12 month stability study at several temperatures and relative humidities for the L-tartarate salt of the compound of formula (IA) wherein $R^2$ and $R^3$ are both OH. As can be seen, substantially no change in chemical purity was observed under any of the conditions tested, and the physical appearance did not change from that of an off-white solid except at the 12 month time point at 25° C., a slight yellowing was observed.

While the invention has been described in conjunction with the detailed description, the foregoing description is intended to illustrate and not limit the scope of the invention, which is defined by the scope of the appended claims. Other aspects, advantages, and modifications are within the scope of the following claims.

What is claimed is:

1. A solid form of a tartrate salt hydrate of a pyrrolidine compound of formula

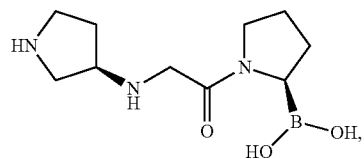

or a cyclic form thereof of formula

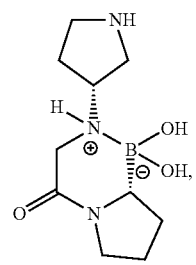

or a mixture thereof, wherein the solid form comprises about 8-14% water by weight and is substantially non-hygroscopic when exposed to atmosphere at a relative humidity of up to 40 to 60% at about 25° C.

2. The tartrate salt hydrate solid form of claim 1 wherein the solid form remains a solid upon standing in air at a relative humidity of 40-60% at 25° C. for a period of about 100 hours, or a period of about three months, or a period of about six months.

3. The tartrate hydrate solid form of claim 1 wherein the tartrate is the L form.

* * * * *

UNITED STATES PATENT AND TRADEMARK OFFICE
CERTIFICATE OF CORRECTION

PATENT NO.       : 8,299,271 B2
APPLICATION NO.  : 12/439140
DATED            : October 30, 2012
INVENTOR(S)      : Wu et al.

It is certified that error appears in the above-identified patent and that said Letters Patent is hereby corrected as shown below:

On the Title page, in column 2, under Item [56] "Other Publications", line 8, delete "Filed" and insert --filed--, therefor On the Title page, in column 2, under Item [56] "Other Publications", line 29, before "Taiwan", insert --"--, therefor On the Title page, in column 2, under Item [56] "Other Publications", line 30, after "May 19, 2010", insert --"--, therefor On the Title page, in column 2, under Item [56] "Other Publications", line 33, delete "Mailed" and insert --mailed--, therefor On the Title page, in column 2, under Item [56] "Other Publications", line 36, delete "Filed:" and insert --filed--, therefor On the Title page, in column 2, under Item [56] "Other Publications", line 49, before "Eurasian", insert --"--, therefor On the Title page, in column 2, under Item [56] "Other Publications", line 51, after "Dec. 27, 2011,", insert --"--, therefor On the Title page, in column 2, under Item [56] "Other Publications", line 52, before "European", insert --"--, therefor On the Title page, in column 2, under Item [56] "Other Publications", line 53, after "Dec. 14, 2011,", insert --"--, therefor Signed and Sealed this
Eighth Day of April, 2014

Michelle K. Lee
*Deputy Director of the United States Patent and Trademark Office*

CERTIFICATE OF CORRECTION (continued)
U.S. Pat. No. 8,299,271 B2

On Title page 2, in column 2, under Item [56] "Other Publications", line 4, after "Korean Application Serial No. 10-2009-7006270, Amendment filed Aug. 23, 2012".", insert --"Australian Application Serial No. 2007290684, Office Action mailed Jan. 13, 2012," 2 pgs.--, therefor In the Specification Column 2, line 8, delete "DPP-1V" and insert --DPP-IV--, therefor Column 5, line 61, delete "DPP-VIM" and insert --DPP-VIII--, therefor Column 8, line 7, delete "infer alio" and insert --inter alia--, therefor Column 9, line 42, delete "ylamino]" and insert --ylamino]- --, therefor Column 10, line 46, delete "glycernic" and insert --glycemic--, therefor Column 12, line 18, before "a", insert --as--, therefor Column 12, line 64, delete "pharrmaceutical" and insert --pharmaceutical--, therefor Column 14, line 48, delete "or' for" and insert --or for--, therefor Column 17, line 5, delete "ofa" and insert --of a--, therefor Column 17, line 8, delete "the" and insert --an--, therefor Column 18, line 17 (Approx.), scheme 1, step 3, delete "t-Butylmehtyl" and insert --t-Butylmethyl--, therefor